(12) United States Patent
Park

(10) Patent No.: US 11,717,263 B2
(45) Date of Patent: Aug. 8, 2023

(54) ALL-IN-ONE MAMMOGRAPHY AND BREAST ULTRASONOGRAPHY APPARATUS

(71) Applicant: MEDICAL PARK CO., LTD., Yongin-si (KR)

(72) Inventor: Hee Boong Park, Seoul (KR)

(73) Assignee: MEDICAL PARK CO., LTD., Yongin-si (KR)

( * ) Notice: Subject to any disclaimer, the term of this patent is extended or adjusted under 35 U.S.C. 154(b) by 10 days.

(21) Appl. No.: 17/580,150

(22) Filed: Jan. 20, 2022

(65) Prior Publication Data

US 2022/0233165 A1    Jul. 28, 2022

(30) Foreign Application Priority Data

Jan. 22, 2021    (KR) .......................... 10-2021-0009513

(51) Int. Cl.
*A61B 6/00* (2006.01)
*A61B 6/04* (2006.01)
*A61B 8/00* (2006.01)
*A61B 8/08* (2006.01)

(52) U.S. Cl.
CPC .......... *A61B 8/4416* (2013.01); *A61B 6/0414* (2013.01); *A61B 6/4447* (2013.01); *A61B 6/502* (2013.01); *A61B 6/5247* (2013.01); *A61B 8/0825* (2013.01); *A61B 8/406* (2013.01); *A61B 8/4444* (2013.01)

(58) Field of Classification Search
None
See application file for complete search history.

(56) References Cited

U.S. PATENT DOCUMENTS

| | | | |
|---|---|---|---|
| 7,963,918 B2 | 6/2011 | Park | |
| 9,636,073 B2 | 5/2017 | Evans et al. | |
| 9,730,659 B2* | 8/2017 | Marcovici | A61B 6/025 |
| 2013/0237814 A1* | 9/2013 | Marcovici | A61B 6/502 |
| | | | 600/436 |
| 2014/0180082 A1* | 6/2014 | Evans | A61B 6/502 |
| | | | 600/436 |

FOREIGN PATENT DOCUMENTS

KR    10-0668766 B1    1/2007

* cited by examiner

*Primary Examiner* — Luther Behringer
(74) *Attorney, Agent, or Firm* — NKL Law; Jae Youn Kim

(57) ABSTRACT

An all-in-one mammography and breast ultrasonography apparatus is provided. The apparatus includes: a scanning table on which breasts are placed, the scanning table having a first axis aligned with a scanning direction of breasts and a second axis orthogonal to the first axis; an X-ray imaging device including an X-ray source arranged above the scanning table to generate X-rays for mammography and an X-ray flat panel detector arranged on the scanning table to detect the X-rays generated from the X-ray source; first and second ultrasound probes arranged on the scanning table so as to be adjacent to both ends of the X-ray flat panel detector to perform breast ultrasonography, the first and second ultrasound probes elongated along the second axis; and an orbital motion device installed on the scanning table to reciprocate the X-ray flat panel detector and the first and second ultrasound probes together along the first axis.

11 Claims, 16 Drawing Sheets

ALL-IN-ONE MAMMOGRAPHY AND BREAST ULTRASONOGRAPHY APPARATUS

CROSS-REFERENCE TO RELATED APPLICATION OF THE INVENTION

The present application claims the benefit of Korean Application No. 10-2021-0009513, filed on Jan. 22, 2021, in the Korean Intellectual Property Office, the disclosure of which is incorporated by reference herein in its entirety.

Technical Field

The present invention relates to a technique for diagnosing breast cancer, and more particularly, to an all-in-one mammography and breast ultrasonography apparatus capable of performing mammography and breast ultrasonography under the same conditions.

Background Art

The most basic tests for diagnosing breast cancer are mammography and breast ultrasonography. Mammography is a method of imaging a breast using X-rays and is used to examine breast cancer by imaging tumors, mammary gland enlargement and fibrosis inside a breast, and microcalcification of a breast. Breast ultrasonography is a method of imaging a breast using ultrasound, and makes it easy to distinguish fat, muscles, and mammary glands inside a breast and to check lesions such as tumors or the like. Breast ultrasonography is mainly used when examining a dense breast with a high mammary gland density or a breast having nodules. Breast ultrasonography has been performed as a secondary examination when abnormal findings are found on mammography. In recent years, breast ultrasonography is also performed as a primary examination together with mammography.

The reason why mammography and breast ultrasonography are performed in parallel is that different kinds of information are obtained from the same object due to the difference in characteristics between X-rays and ultrasound. For example, in the case of mammography, it is difficult to distinguish between a mammary gland and a tumor, and it is difficult to identify an accurate lesion in a dense breast. Therefore, in mammography, the lesion is inferred through microcalcification. Breast ultrasonography is capable of distinguishing a mammary gland from a tumor, which makes it possible to accurately identify a lesion. However, it is difficult to identify microcalcification. In general, ultrasound equipment for breast ultrasonography is composed of a handheld type in which medical staff directly hold and use the ultrasound equipment with their hands. In the case of handheld type ultrasound equipment, the image of the breast may be taken differently depending on the skill level of the medical staff. Therefore, it is difficult to diagnose breast cancer uniformly and accurately because there are variations in the accuracy of the location of a breast cancer lesion.

"Apparatus for ultrasonic examination of deformable object" disclosed in Korean Patent No. 10-0668766 (U.S. Pat. No. 7,963,918 B2) includes: a frame; a caterpillar having a flat surface on which a deformable object with rigidity in the width direction is placed, the caterpillar installed on the frame to move forward and backward with a constant movable distance in the longitudinal direction; a driving means for moving the caterpillar forward and backward; and at least one ultrasound probe arranged long in the width direction of the caterpillar, so that the ultrasound transmission/reception surface is located on the substantially same plane as the upper surface of the caterpillar, and fixed to the caterpillar so that the ultrasound probe is located more inward from both sides in the longitudinal direction than the movable distance of the upper surface of the caterpillar. The apparatus disclosed in this patent document has an advantage in that an ultrasound examination can be performed while moving the ultrasound probe in a state in which the position and shape of an object are maintained.

"Dual-Modality Mammography" disclosed in U.S. Pat. No. 9,636,073 B2 is configured to implement mammography and breast ultrasonography using one scanner. The scanning assembly includes a housing configured to define a scanning surface, an ultrasound transducer mounted inside the housing so that it can move on a plane parallel to the scanning surface to image biological tissue, and an X-ray detector mounted inside the housing to take X-ray images by X-rays passing through biological tissue from an X-ray source. The X-ray detector may be configured as a linear slot X-ray detector or a flat panel detector. The dual-modality mammography disclosed in this patent document has an advantage in that mammography and breast ultrasonography can be performed by a single scanner. The contents disclosed in the above patent documents are incorporated herein by reference.

As described above, Korean Patent No. 10-0668766 discloses that breast ultrasonography can be performed while the ultrasound probe is moved by the caterpillar. However, mammography cannot be performed. Therefore, there is a problem that a separate mammography apparatus is required. In addition, since the X-ray image of the mammography apparatus and the ultrasound image of the breast ultrasonography are acquired under the condition in which the position and pressing level of the breast are different, there is a limitation in accurately examining a lesion by matching the two images.

U.S. Pat. No. 9,636,073 B2 discloses that mammography using an X-ray source and an X-ray detector and breast ultrasonography using an ultrasound transducer can be performed by one scanner. However, as the scanning distance, i.e., the feeding distance of the ultrasound transducer for mammography increases, the length of the housing increases and the size of the driver for moving the ultrasound transducer also increases. Therefore, there is a problem in that the size and weight of the scanner are increased, thereby lowering the operability, and increasing the manufacturing cost. In addition, as the scanning distance increases, the time required for breast ultrasonography increases, which leads to a problem in that the efficiency of breast cancer examination is reduced.

SUMMARY

In view of the problems inherent in the mammography and the breast ultrasonography mentioned above, it is an object of the present invention to provide a novel all-in-one mammography and breast ultrasonography apparatus that can perform mammography by an X-ray imaging device and breast ultrasonography by two ultrasound probes arranged on both sides of an X-ray flat panel detector, under the same condition.

Another object of the present invention is to provide a novel all-in-one mammography and breast ultrasonography apparatus that can perform breast ultrasonography for each of left and right breasts by each of two ultrasound probes arranged on both sides of an X-ray flat panel detector, thereby shortening the scanning distance, reducing the size and weight of the apparatus, improving the operability, and enhancing the efficiency of breast cancer examination.

A further object of the present invention is to provide a novel all-in-one mammography and breast ultrasonography apparatus that has a simple structure for enabling an X-ray flat panel detector and two ultrasound probes to scan breasts according to the orbital motion of an orbital motion device, thereby enhancing the productivity, and reducing the manufacturing cost.

A still further object of the present invention is to provide a novel all-in-one mammography and breast ultrasonography apparatus in which an X-ray flat panel detector and two ultrasound probes are mounted on a carriage to move together, thereby reducing a position error between an X-ray image and an ultrasound image acquired in the apparatus.

A yet still further object of the present invention is to provide a novel all-in-one mammography and breast ultrasonography apparatus in which a caterpillar for moving an X-ray flat panel detector and two ultrasound probes together can firmly support pressed breasts.

An even yet still further object of the present invention is to provide a novel all-in-one mammography and breast ultrasonography apparatus that can freely adjust the height and orientation thereof according to the body type and the examination area of a subject.

According to one aspect of the present invention, there is provided an all-in-one mammography and breast ultrasonography apparatus. The all-in-one mammography and breast ultrasonography apparatus according to the present invention includes: a scanning table on which breasts are placed, the scanning table having a first axis aligned with a scanning direction of breasts and a second axis orthogonal to the first axis; an X-ray imaging device including an X-ray source arranged above the scanning table to generate X-rays for mammography and an X-ray flat panel detector arranged on the scanning table to detect the X-rays generated from the X-ray source; first and second ultrasound probes arranged on the scanning table so as to be adjacent to both ends of the X-ray flat panel detector to perform breast ultrasonography, the first and second ultrasound probes elongated along the second axis; and an orbital motion device installed on the scanning table to reciprocate the X-ray flat panel detector and the first and second ultrasound probes together along the first axis.

In the all-in-one mammography and breast ultrasonography apparatus according to the present invention, the orbital motion device may include: a carriage arranged on the scanning table to reciprocate along the first axis and having an upper surface on which the X-ray flat panel detector is mounted and on which the first and second ultrasound probes are mounted so as to be adjacent to both ends of the X-ray flat panel detector; a pair of caterpillars connected at one ends to both ends of the carriage so as to reciprocate the carriage along the first axis and including a plurality of links elongated along the second axis; a pair of sliding plates arranged on the scanning table to reciprocate along the first axis and connected to the other ends of caterpillars; and a horizontal linear actuator configured to drive the caterpillars along the first axis. The orbital motion device is configured to simultaneously move the X-ray flat panel detector and the first and second ultrasound probes and is configured to firmly support the breasts pressed against the scanning surface of the scanning table by the caterpillars.

The all-in-one mammography and breast ultrasonography apparatus according to the present invention can accurately and easily perform mammography by the X-ray imaging device and breast ultrasonography by the two ultrasound probes arranged on both sides of the X-ray flat panel detector, under the same condition, thereby shortening the scanning distance, reducing the size and weight of the apparatus, improving the operability, and enhancing the efficiency of breast cancer examination. Further, the all-in-one mammography and breast ultrasonography apparatus has the simple structure for enabling the X-ray flat panel detector and the two ultrasound probes to scan breasts according to the orbital motion of the orbital motion device, thereby enhancing the productivity, and reducing the manufacturing cost. Further, in the all-in-one mammography and breast ultrasonography apparatus, the X-ray flat panel detector and the two ultrasound probes are mounted on the carriage of the orbital motion device to move together, thereby reducing the position error between the X-ray image and the ultrasound image acquired in the apparatus and enhancing the examination accuracy. Further, in the all-in-one mammography and breast ultrasonography apparatus, the caterpillar for moving the X-ray flat panel detector and the two ultrasound probes together can firmly support pressed breasts, thereby reducing the error caused by the deformation of the breasts. Further, the all-in-one mammography and breast ultrasonography apparatus can freely adjust the height and orientation of the scanning table according to the body type and the examination area of the subject, thereby enhancing the ease of use.

DETAILED DESCRIPTION

Figure 1:
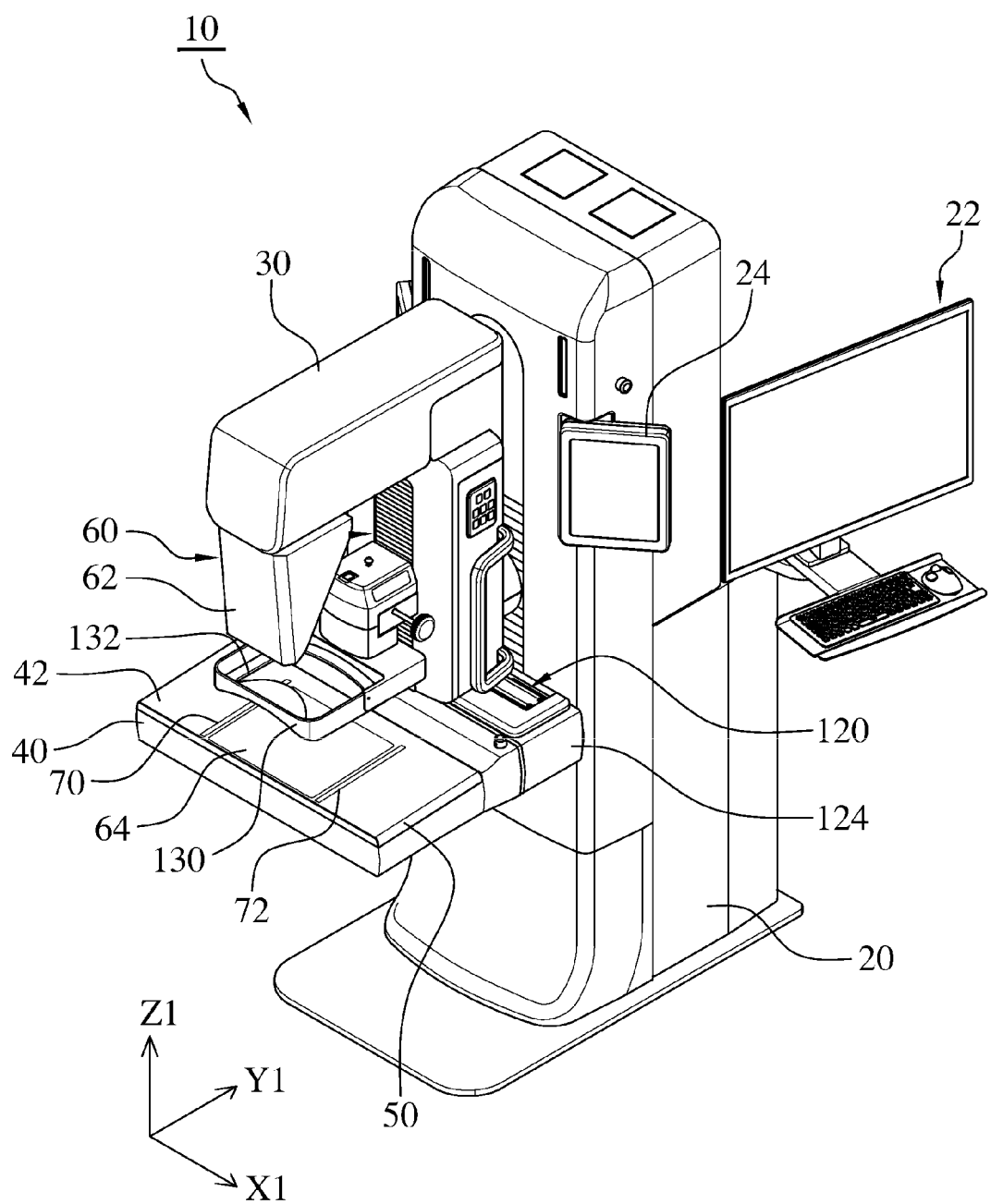
FIG. 1 is a perspective view showing an all-in-one mammography and breast ultrasonography apparatus according to the present invention.
Figure 2:
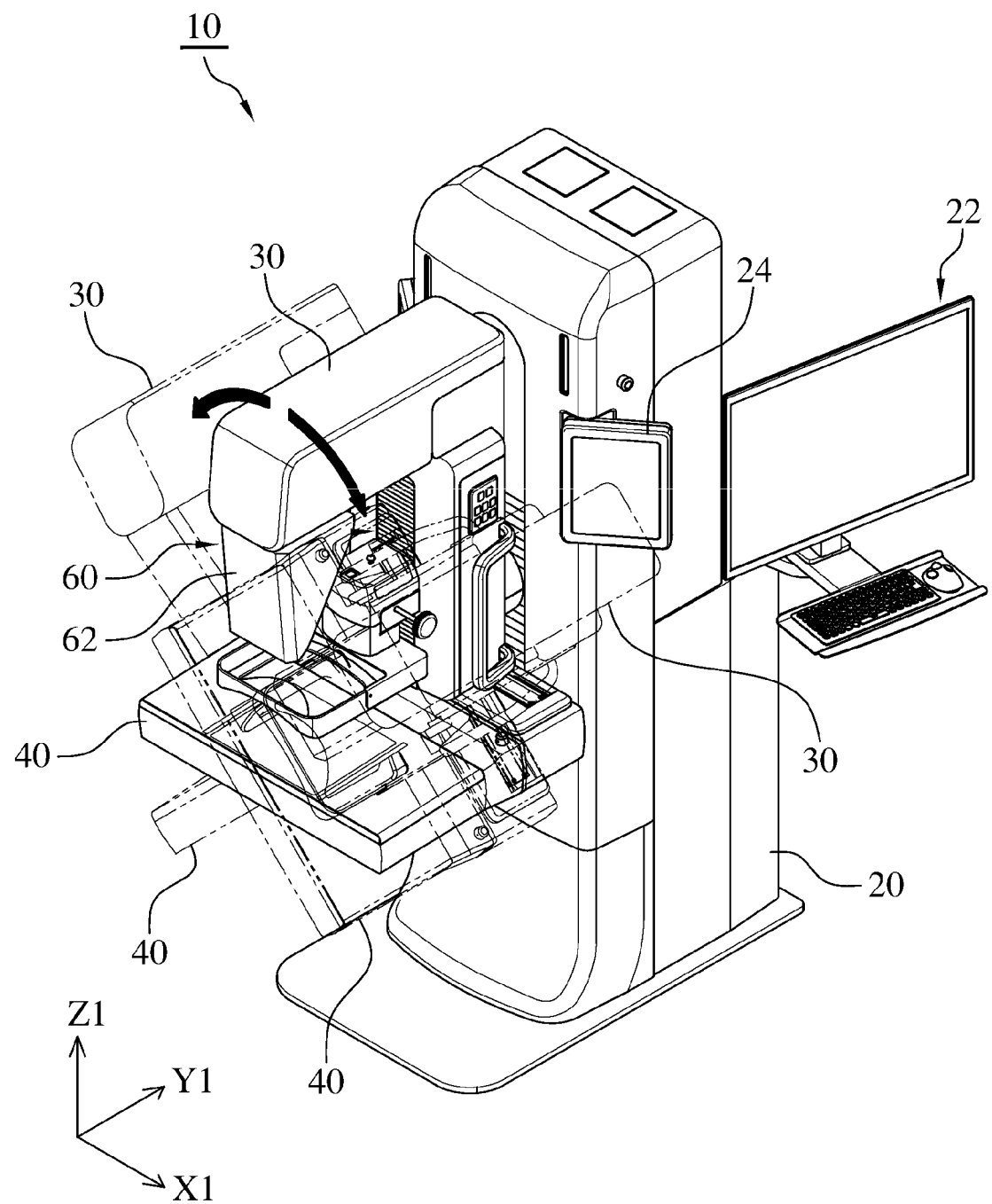
FIG. 2 is a perspective view showing an operation of a gantry in the apparatus according to the present invention.
Figure 3:
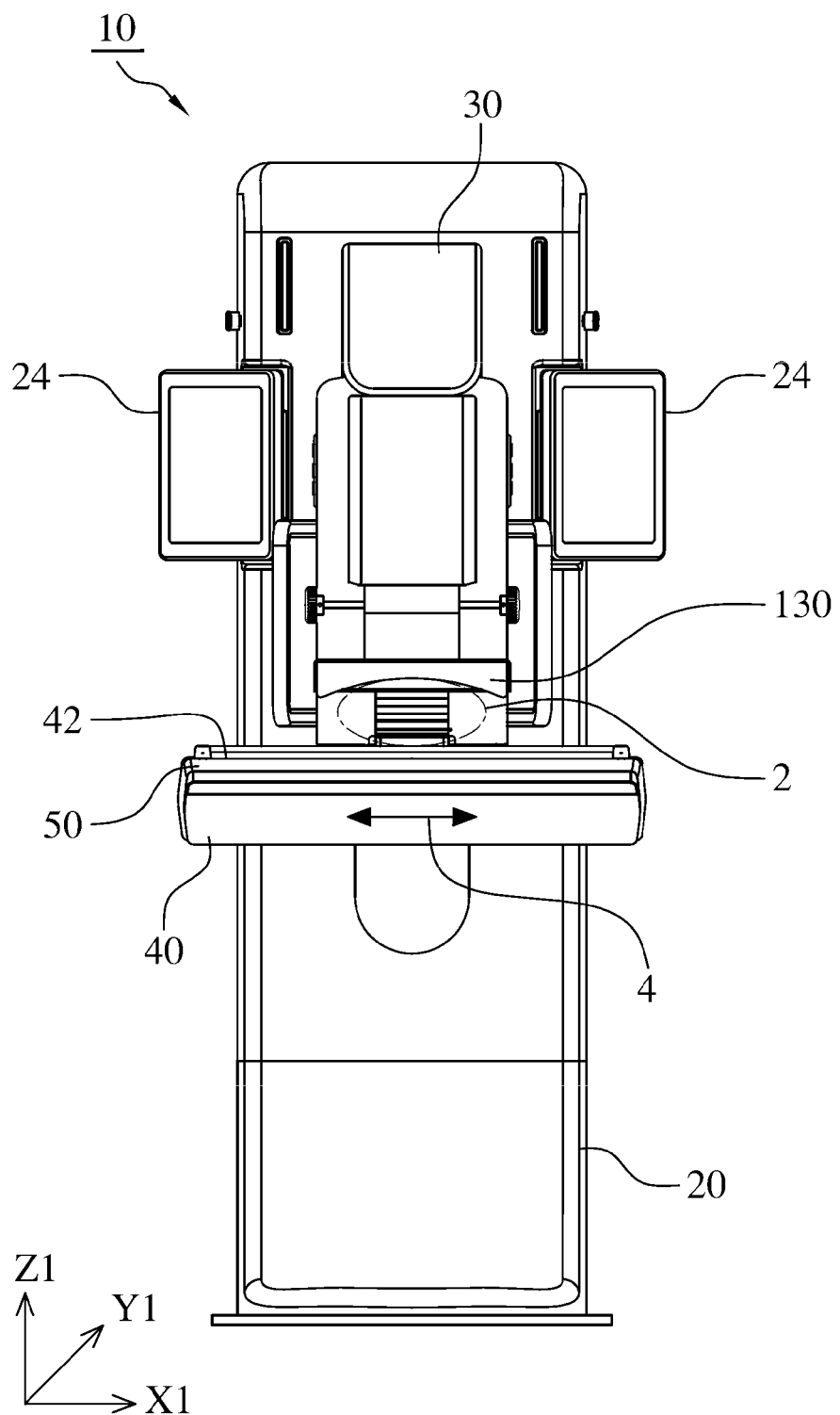
FIG. 3 is a front view showing the apparatus according to the present invention.
Figure 4:
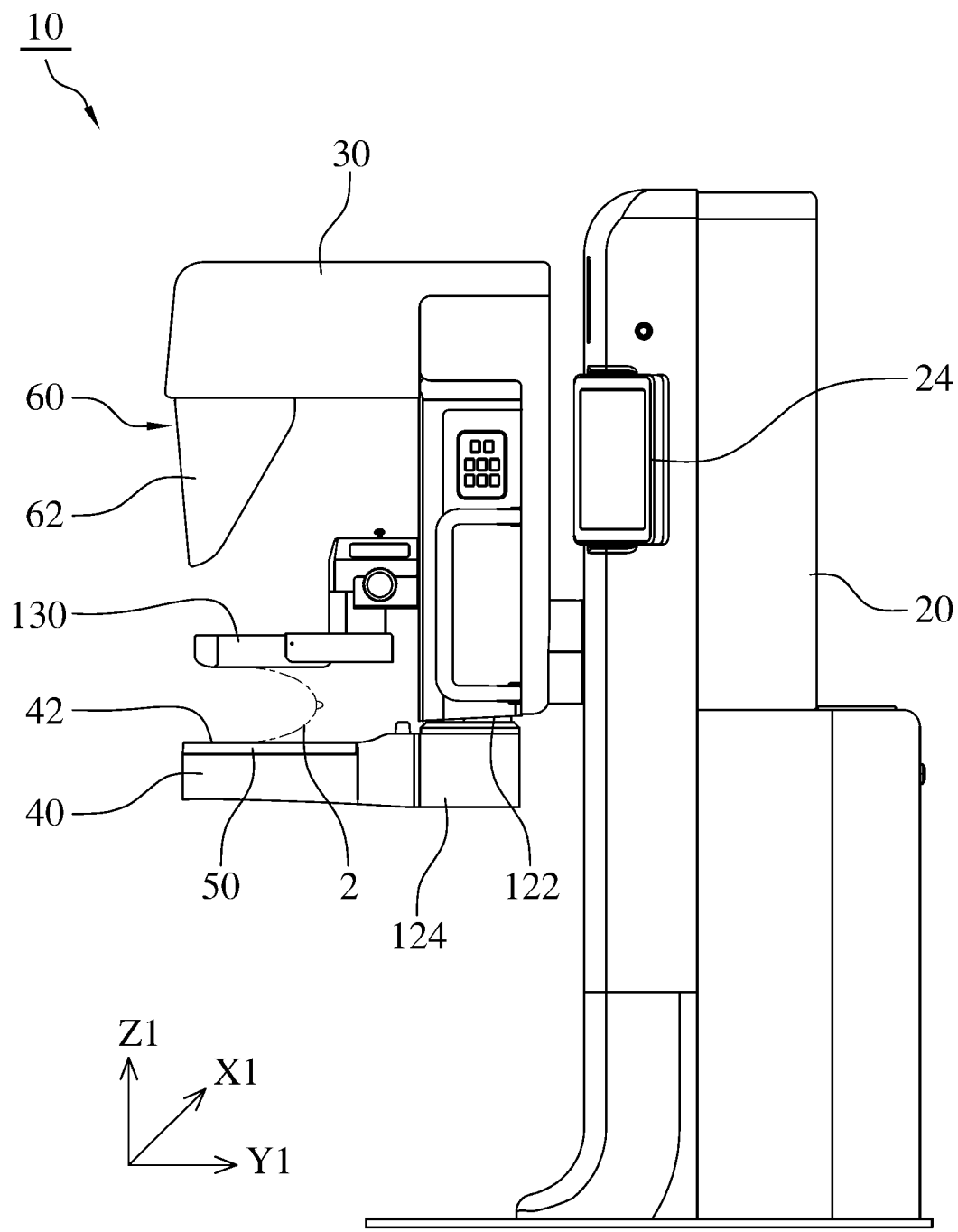
FIG. 4 is a side view showing the apparatus according to the present invention.
Figure 5:
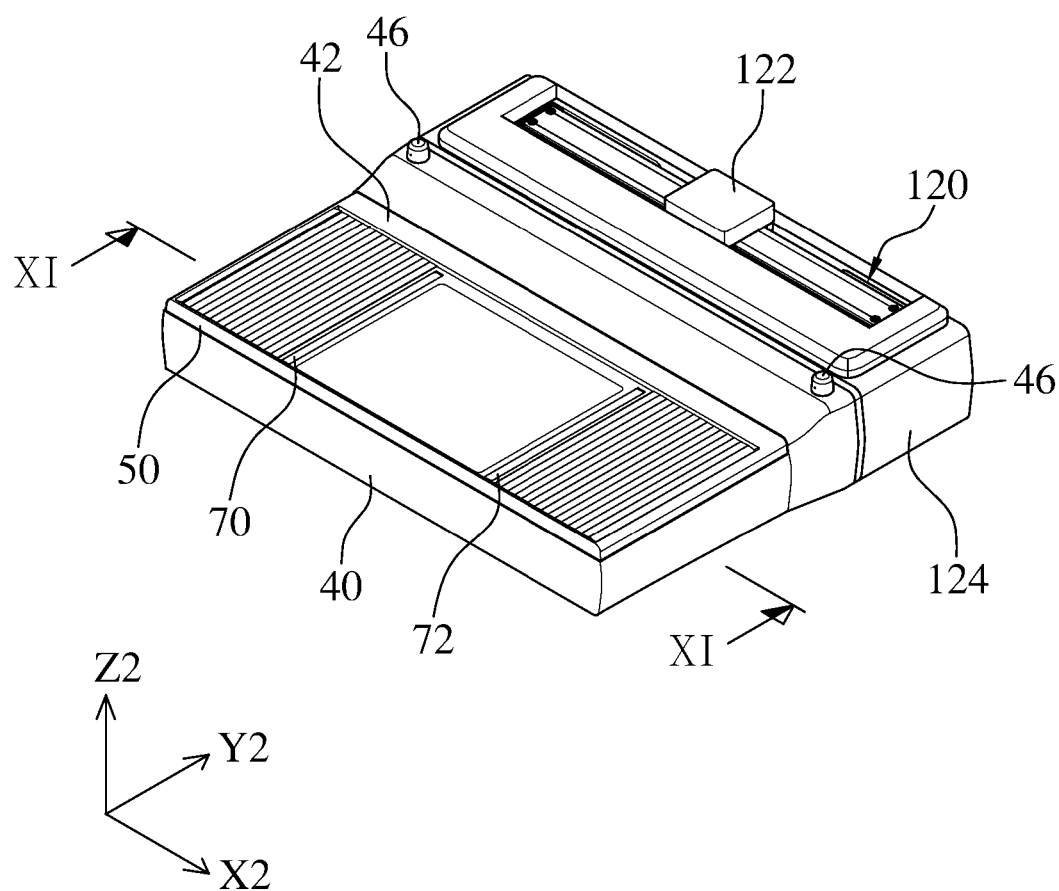
FIG. 5 is a perspective view showing a scanning table of the apparatus according to the present invention.
Figure 6:
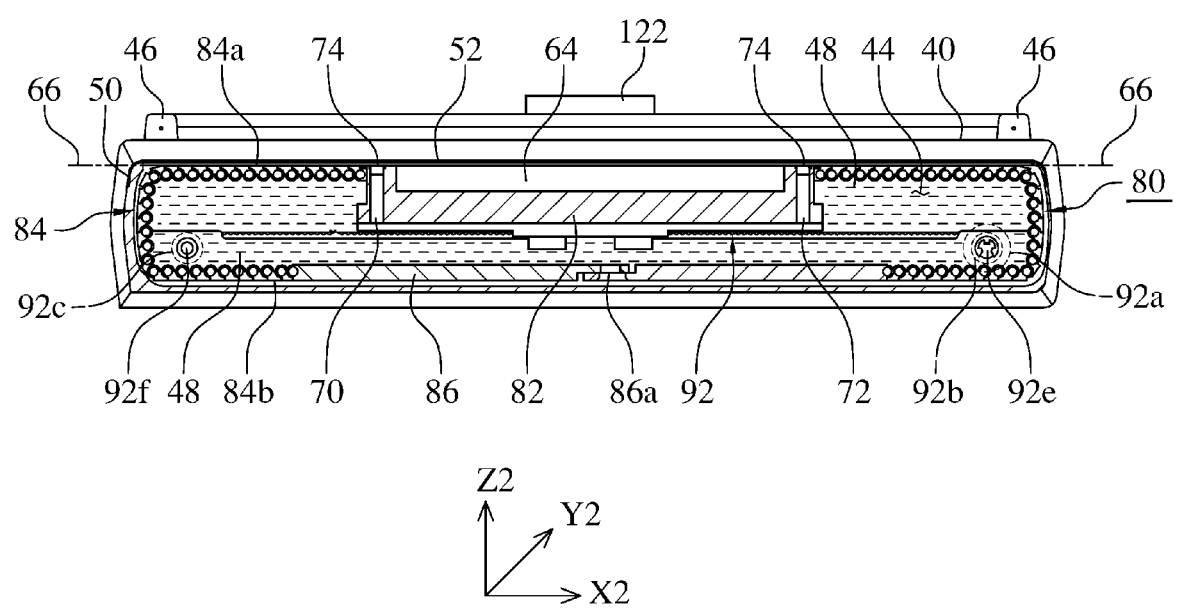
FIG. 6 is a plan view showing the scanning table of the apparatus according to the present invention.
Figure 7:
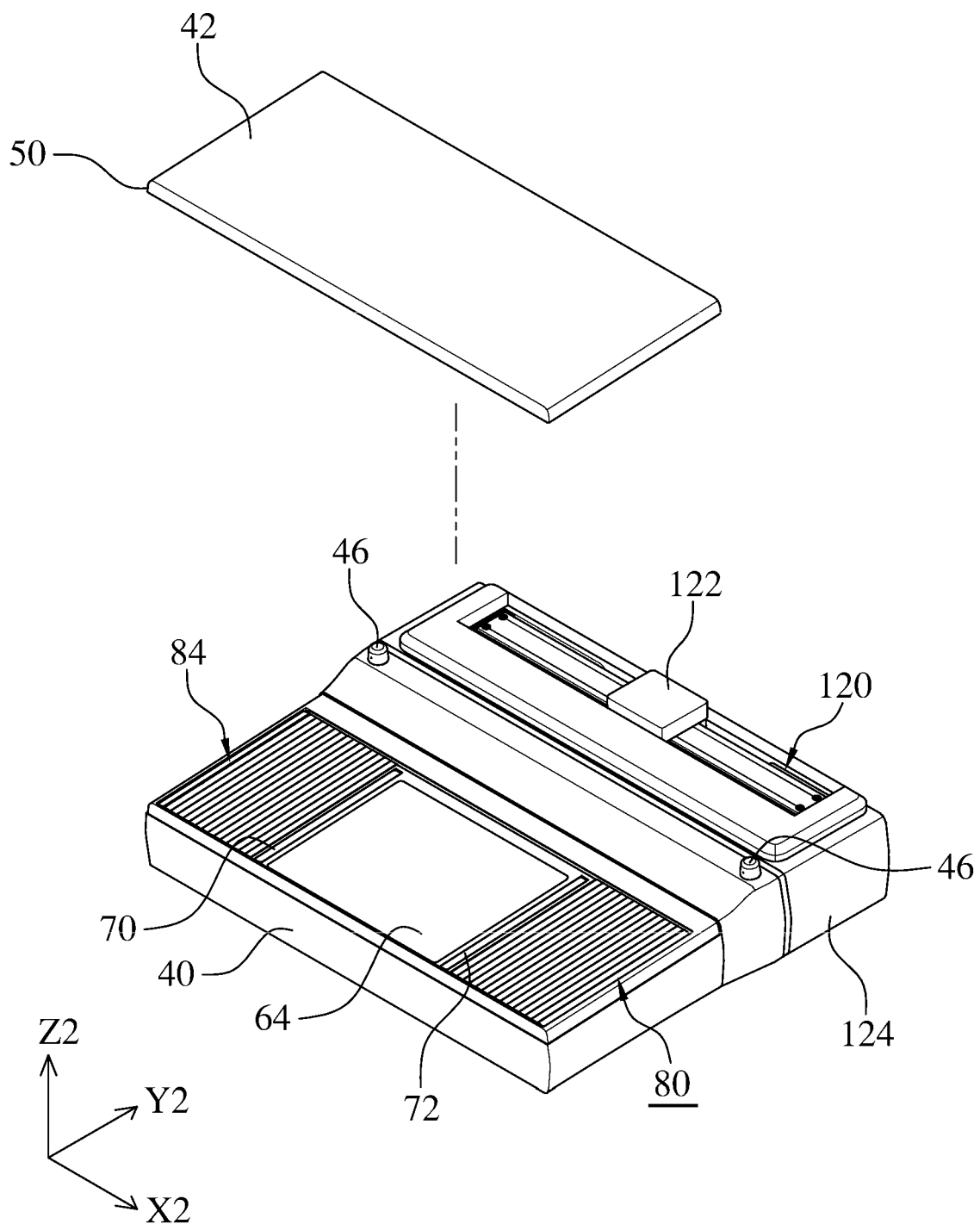
FIG. 7 is a sectional view taken along line VII-VII in FIG. 6.
Figure 8:
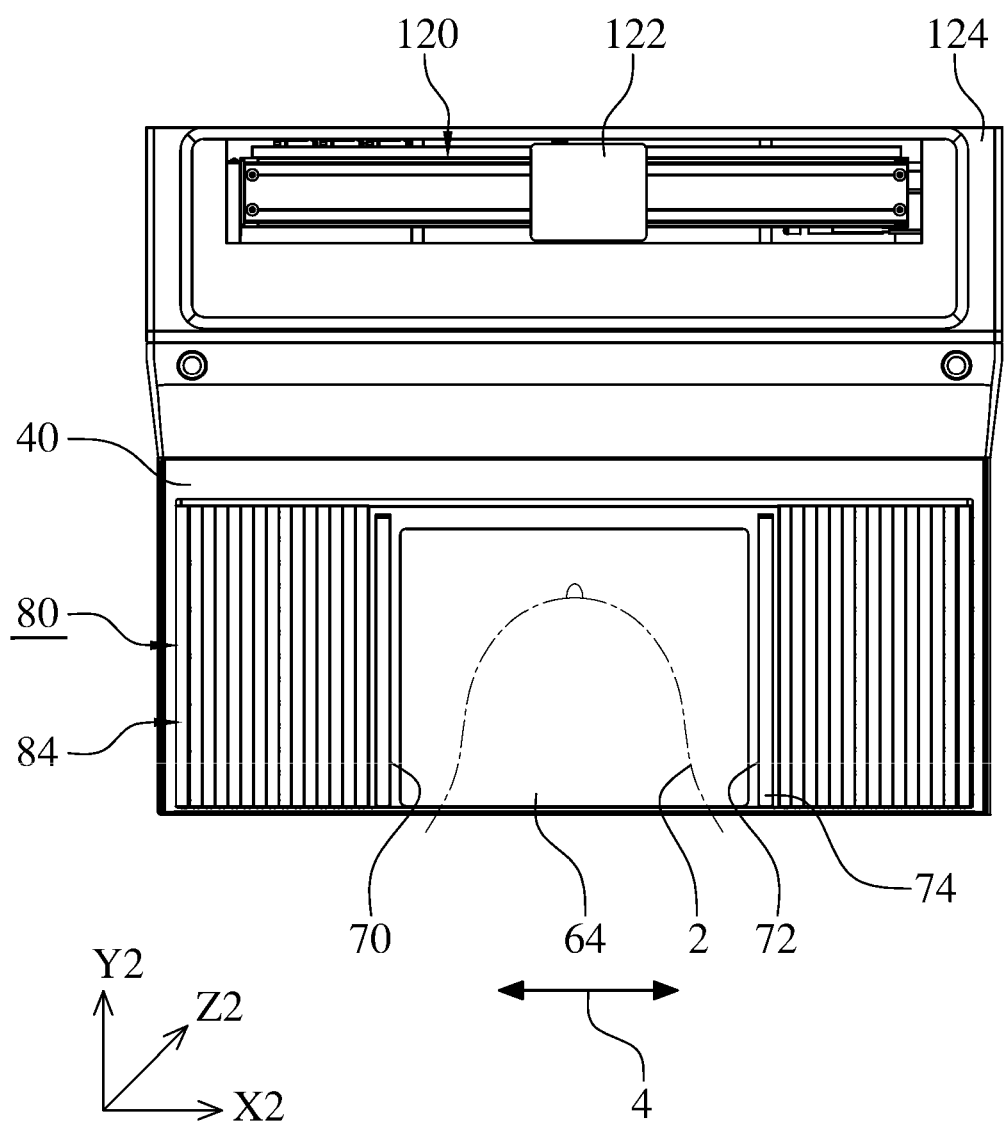
FIG. 8 is a perspective view showing the scanning table and the flat cover separated from each other in the apparatus according to the present invention.
Figure 9:
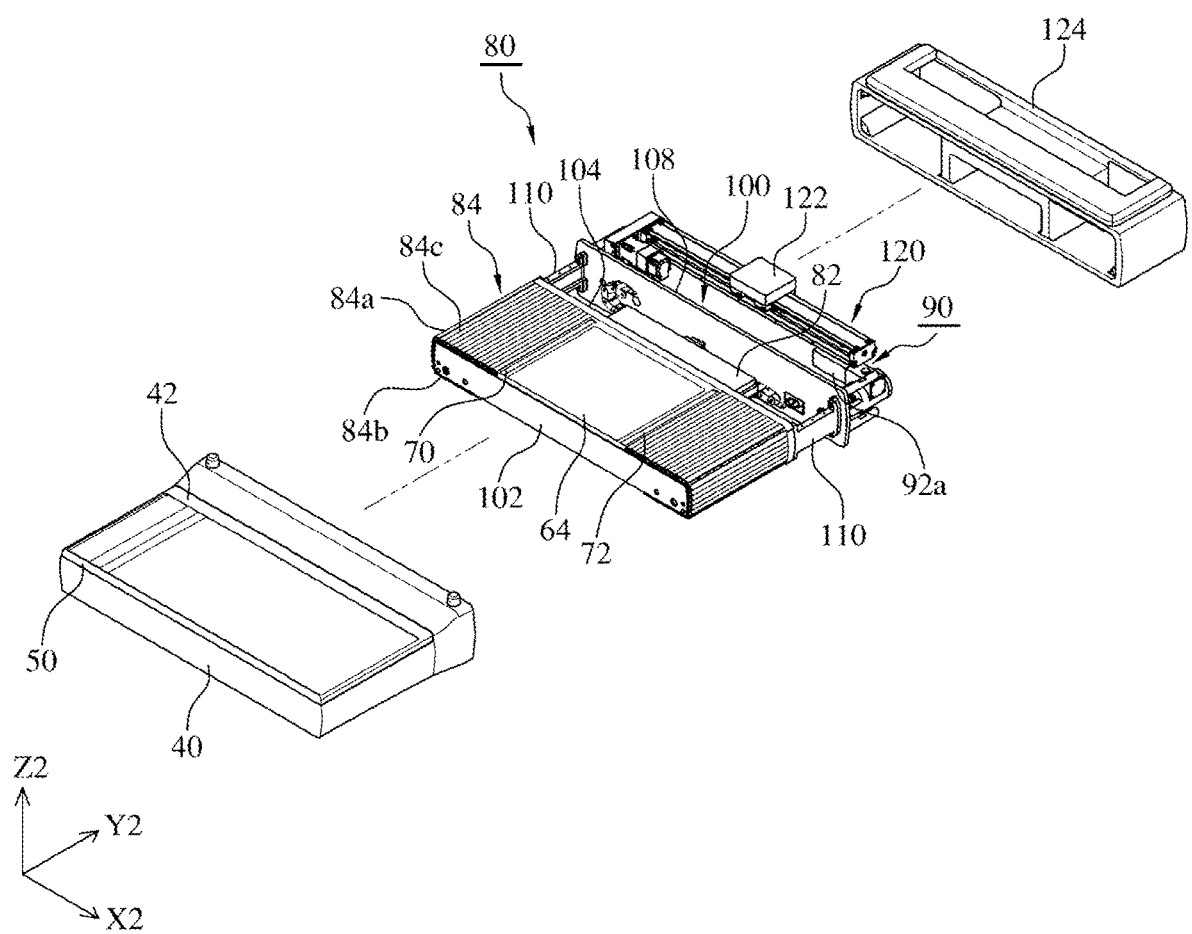
FIG. 9 is a perspective view showing the scanning table and the inner frame separated from each other in the apparatus according to the present invention.
Figure 10:
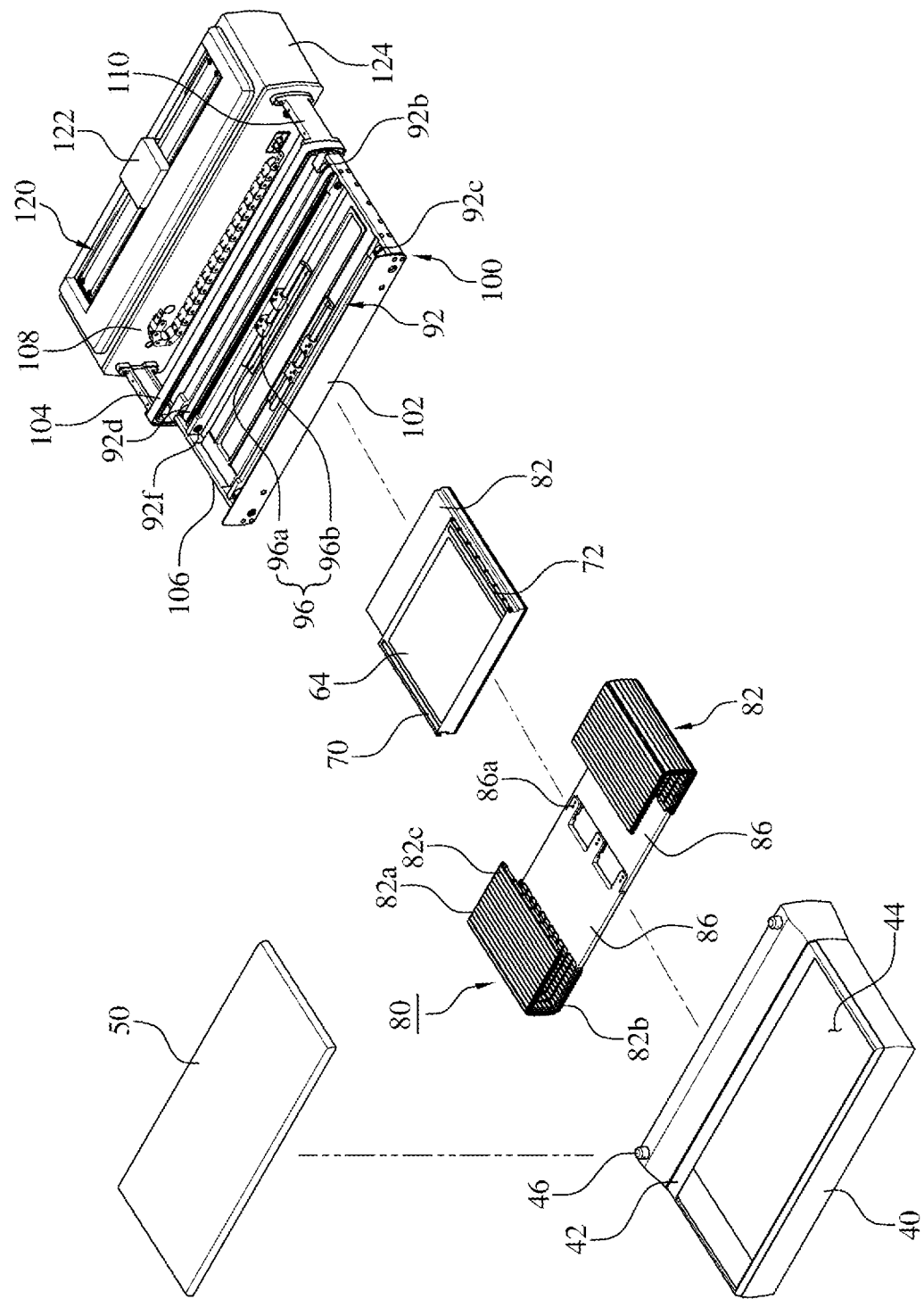
FIG. 10 is a perspective view showing the scanning table, the orbital motion device, the X-ray flat panel detector, the first and second ultrasound probes and the inner frame separated from each other in the apparatus according to the present invention.
Figure 11:
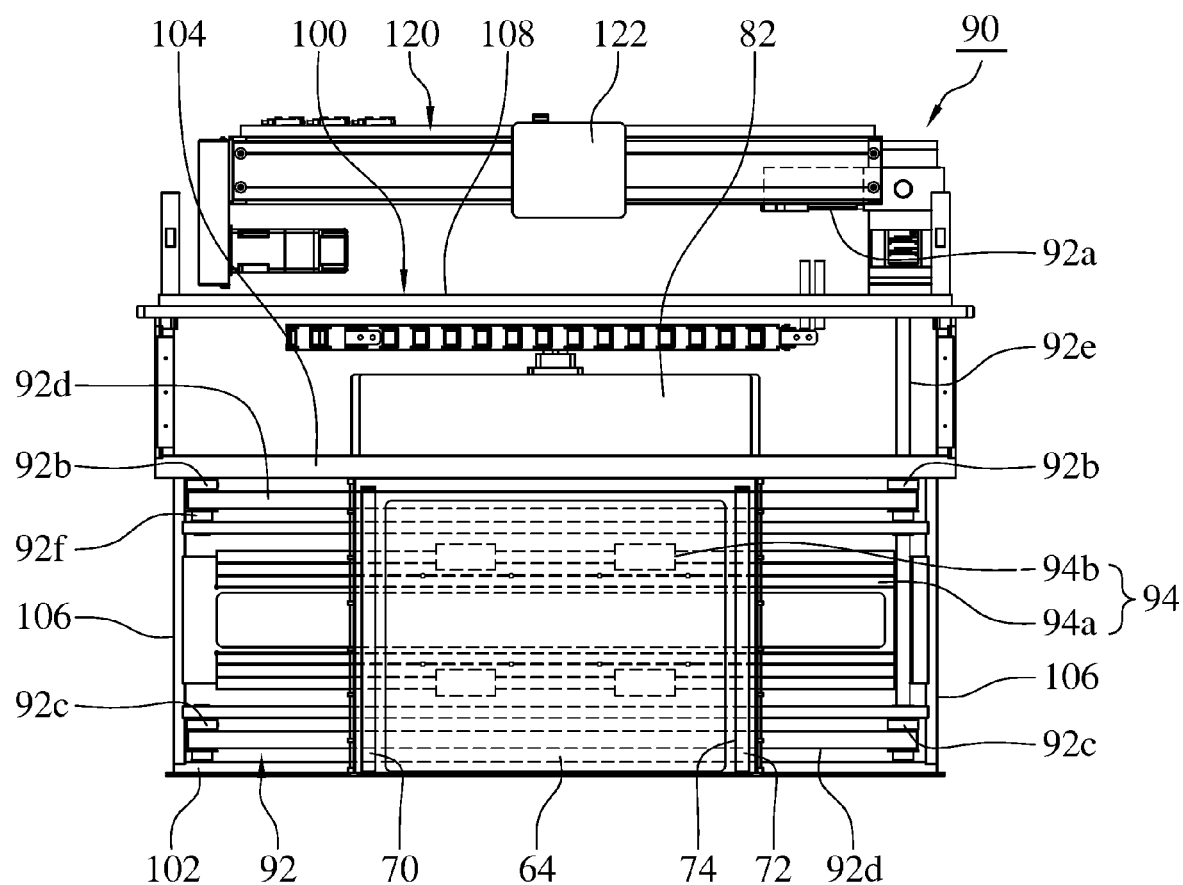
FIG. 11 is a plan view illustrating the orbital motion device, the X-ray flat panel detector, the first and second ultrasound probes and the inner frame in the apparatus according to the present invention.

Other objects, specific advantages and novel features of the present invention will become more apparent from the following detailed description and preferred embodiments taken in conjunction with the accompanying drawings. In describing the present invention, the size or shape of the components shown in the drawings may be exaggerated or simplified for clarity and convenience of description. In addition, the terms specifically defined in consideration of the configuration and operation of the present invention may vary depending on the intention or custom of a user or an operator. These terms should be interpreted as meanings and concepts consistent with the technical spirit of the present invention based on the contents throughout this specification.

Hereinafter, preferred embodiments of the all-in-one mammography and breast ultrasonography apparatus according to the present invention will be described in detail with reference to the accompanying drawings.

Referring first to FIGS. 1 to 4, the all-in-one mammography and breast ultrasonography apparatus 10 according to the present invention includes an upright stand 20 and a gantry 30 arranged on the front side of the upright stand 20. The upright stand 20 has a first axis X1, a second axis Y1 orthogonal to the first axis X1, and a third axis Z1 orthogonal to the first axis X1 and the second axis Y1. The upright stand 20 is composed of a hollow housing. The upright stand 20 may be configured as a portable upright stand that can be freely moved by a plurality of casters. A computer device 22 or a central processing unit (CPU) is installed on one side of the upright stand 20 so as to process an X-ray image and an ultrasound image by a program. A display 24 is mounted on the upright stand 20 so as to be connected to the computer device 22. The gantry 30 is connected to the front side of the upright stand 20 so as to make translational motion along the third axis Z1 direction (height direction) and make rotational motion about the second axis Y1.

The actuator means for providing a driving force for the Z-axis translational motion, i.e., the lifting of the gantry 30 may be composed of a vertical linear actuator (not shown) such as a chain transmission mechanism, a lead screw linear actuator, a belt driven linear actuator, a rack and pinion actuator, or the like, which is mounted inside the upright stand 20. The actuator means for providing a driving force for the Y-axis rotational motion of the gantry 30 may be composed of a rotary actuator (not shown) such as an electric motor, a pneumatic motor, or the like, which is mounted inside the upright stand 20.

Referring to FIGS. 1 to 7, the apparatus 10 according to the present invention includes a scanning table 40 disposed under the gantry 30 so that the breasts 2 can be placed on the scanning table 40 for mammography and breast ultrasonography. The scanning table 40 has a first axis X2 (longitudinal direction) aligned with the scanning direction 4 of each breast 2, a second axis Y2 (width direction) orthogonal to the first axis X2, and a third axis Z3 orthogonal to the first axis X2 and the second axis Y2. The scanning table 40 defines a scanning surface 42 on which the breasts 2 are placed and includes a casing having a closed chamber 44. A pair of liquid injection ports 46 are respectively coupled to both sides of the upper surface of the scanning table 40.

Liquid 48, for example, deionized water or non-conductive liquid as a medium (acoustic coupling medium) for transmission of X-rays and propagation of ultrasound waves is filled in the chamber 44 through the liquid injection ports 46. Deionized water prevents attenuation and refraction of ultrasound waves, thereby improving the reliability of breast ultrasonography. Deionized water may flow out of the chamber 44 through the liquid injection ports 46. A phenomenon in which air bubbles affect an ultrasound image when an air pocket is generated in the chamber 44 can be prevented by forming the liquid injection ports 46 on both sides of the upper surface of the scanning table 40 to allow injection and discharge of deionized water. A flat cover 50 is mounted on the upper surface of the scanning table 40 to form a scanning surface 42 for placing and scanning the breasts 2. The cover 50 has transmittance enough to transmit X-rays and ultrasound waves. The cover 50 may be made of a polymethyl pentene film having excellent transmittance of ultrasound waves.

Referring to FIGS. 1 to 12, the apparatus 10 according to the present invention includes an X-ray imaging device 60 for mammography. The X-ray imaging device 60 includes an X-ray source 62 and an X-ray flat panel detector 64. The X-ray source 62 or an X-ray generator or an X-ray tube is mounted on the upper side of the gantry 30 so as to be arranged above the scanning table 40. The X-ray flat panel detector 64 or a two-dimensional X-ray detector is arranged at the upper portion of the chamber 44 so as to reciprocate along the first direction X1. The upper surface of the X-ray flat panel detector 64 is aligned with an arbitrary horizontal plane 66 parallel to the scanning surface 42. The X-ray flat panel detector 64 may have a width of 300 mm and a length of 240 mm.

The apparatus 10 according to the present invention includes first and second ultrasound probes 70 and 72 for breast ultrasonography. The first and second ultrasound probes 70 and 72 are arranged to be adjacent to both ends of the X-ray flat panel detector 64 and are elongated in the second axis Y2 direction. The reception/transmission surface 74 of each of the first and second ultrasound probes 70 and 72 is arranged on a horizontal plane 66 that is substantially flush with the upper surface of the X-ray flat panel detector 64. Each of the first and second ultrasound probes 70 and 72 may have a width of 10 mm and a length of 240 mm. Each of the first and second ultrasound probes 70 and 72 is configured as a phased array type probe. In the phased array method, a plurality of elements is formed in a probe to perform breast ultrasonography by electronic scanning.

As shown in FIGS. 6 to 12, the apparatus 10 according to the present invention includes an orbital motion device 80 mounted inside the scanning table 50 so as to reciprocate the X-ray flat panel detector 64 and the ultrasound probes 70 and 72 together along the first axis X2 of the scanning table 50. The orbital motion device 80 includes a carriage 82, a pair of caterpillars 84, a pair of sliding plates 86, and a horizontal linear actuator 90.

The carriage 82 is mounted inside the scanning table 50 so as to reciprocate along the first axis X2. The X-ray flat panel detector 64 is mounted at the center of the upper surface of the carriage 82. The first and second ultrasound probes 70 and 72 are respectively mounted on both edges of the upper surface of the carriage 82 so as to be adjacent to both ends of the X-ray flat panel detector 64.

Each of the caterpillars 84 is mounted inside the scanning table 50 so as to reciprocate the carriage 82 by orbital motion along the first axis X2. One end of each of the caterpillars 84 is connected to each of both ends of the carriage 82. Each of the caterpillars 84 includes an upper track 84*a* flatly arranged on the upper side, and a lower track 84*b* horizontally arranged below the upper track 84*a* at a distance from the upper track 84*a*. The upper surface of the upper track 84*a* may be arranged flatly or horizontally on an arbitrary horizontal plane 66 that is substantially flush with the upper surfaces of the X-ray flat panel detector 64 and the first and second ultrasound probes 70 and 72. The flat upper track 84*a* supports the breasts 2 pressed against the cover 52, for example, a polymethyl pentene film to prevent deformation of the cover 52 and maintains the pressed state of the breasts 2. Each of the caterpillars 84 is formed by the connection of a plurality of links 84*c* which are elongated along the second axis Y2. The upper surface of each of the links 84*c* is formed to be flat and has rigidity along the second axis Y2.

Each of the sliding plates 86 is arranged below the chamber 44 so as to reciprocate along the first axis X2. The sliding plates 86 are connected to each other by a hinge 86*a*. The other end of each of the caterpillars 84 is connected to each of the sliding plates 86 so as to interlock with each of the sliding plates 86.

The horizontal linear actuator 90 or an X-axis linear actuator includes a belt transmission device 92 and a horizontal linear motion guide 94. The belt transmission device 92 is mounted inside the scanning table 50 along the first axis X2 to provide a driving force for orbital motion of the caterpillars 84. The belt transmission device 92 includes a driving motor 92*a*, a pair of driving pulleys 92*b*, a pair of driven pulleys 92*c*, and a pair of belts 92*d*.

The driving motor 92*a* is mounted on one side of the back surface of the scanning table 50 to provide a driving force and may be configured as an electric motor. The driving pulleys 92*b* are connected to the driving motor 92*a* by a driving shaft 92*e* so as to be rotated by the driving force of the driving motor 92*a* and are mounted on one side inside the scanning table 50 so as to be adjacent to the caterpillars 84. The driven pulleys 92*c* are mounted on one side inside the scanning table 50 so as to be able to rotate adjacent to both sides of each of the caterpillars 84 and are connected to each other by a driven shaft 92*f*. The belts 92*d* travels while being wound around the driving pulleys 92*b* and the driven pulleys 92*c*. The belts 92*d* may be configured as timing belts. The carriage 82 is fixed to one side of the belts 92*d* so that it can be moved together with the belts 92*d*. The carriage 82 is fixed to the lower tracks 82*b* of the caterpillars 84. In some embodiments, the belt transmission device 92 may be configured as a lead screw linear actuator, a pinion actuator, or the like that can reciprocate the carriage 82 along the first axis X2.

The horizontal linear motion guide 94 is mounted inside the scanning table 50 so as to allow the carriage 82 to reciprocate in a linear motion along the X-axis direction. The horizontal linear motion guide 94 includes a pair of guide bars 94*a* and a plurality of sliders 94*b*. The guide bars 94*a* are mounted on the bottom of the scanning table 50 side by side along the X-axis direction. The sliders 94*b* are mounted to slide along each of the guide bars 94*a* and are coupled to the carriage 82. Each of the sliders 94*b* is coupled to each of the sliding plates 86 so as to guide the orbital motion of the caterpillar 84 into a linear motion. In some embodiments, the horizontal linear motion guide 94 may be configured as a monorail type linear motion guide having a guide rail and a slider sliding along the guide rail.

The apparatus 10 according to the present invention further includes an inner frame 100 configured to be mounted inside the chamber 44 of the scanning table 40 while holding the components of the orbital motion device 80 such as the carriage 82, the pair of caterpillars 84, the pair of sliding plates 86 and the horizontal linear actuator 90. The inner frame 100 includes front and rear spacer plates 102 and 104, a pair of side plates 106, a rear cover plate 108, and a pair of joint plates 110.

The inner frame 100 is configured in the form of a casing or a housing with an open top. Each of the front and rear spacer plates 102 and 104 is mounted between both ends of the upper and lower tracks 92*a* and 92*b* so as to maintain the spacing between the upper and lower tracks 92*a* and 92*b*. Each of the side plates 106 is arranged inside each of the caterpillars 84 to connect each of the front and rear spacer plates 106. The rear cover plate 108 is spaced apart from the rear spacer plate 104. The joint plates 110 are arranged on both sides between the rear spacer plate 104 and the rear cover plate 108 to connect the rear spacer plate 104 and the rear cover plate 108. The ease of assembly and the rigidity can be improved by modularization in which the orbital motion device 80 is mounted on the inner frame 100.

The apparatus 10 according to the present invention further includes a table positioning linear actuator 120 configured to translationally move the scanning table 50 along the first axis X2 during mammography and breast ultrasonography. The table positioning linear actuator 120 adjusts the position of the scanning table 50 according to the body type of the subject and the positions of the breasts 2. The table positioning linear actuator 120 translationally moves the scanning table 50 along the first axis X2 based on a connector 122 or a joint connected to the gantry 30. The table positioning linear actuator 120 or an X-axis linear actuator is mounted on the back side of the scanning table 50 and may be configured as a lead screw linear actuator, a belt-driven linear actuator, a chain-driven linear actuator, or a rack and pinion actuator. A housing 124 is mounted on the back side of the scanning table 50 to accommodate the table positioning linear actuator 120.

Referring to FIGS. 1 to 4 and 12, the apparatus 10 according to the present invention further includes a press plate 130 for pressing the breasts 2 against the scanning table 50. The press plate 130 is arranged in front of the gantry 30 to press the breasts 2 by translational movement along the third axis Z1. The press plate 130 is arranged between the X-ray source 42 and the X-ray flat plate detector 64. A window 132 is formed at the center of the press plate 130 to transmit the X-rays irradiated from the X-ray source 42. For the transmission of X-rays and the propagation of ultrasound waves, a gel pad coated with a medium material, for example, semi-solid gel, may be mounted on the upper surface of the press plate 130 to cover the window 132. The press plate 130 is translationally moved by the operation of a vertical linear actuator (not shown) such as a lead screw linear actuator, a belt-driven linear actuator, a chain-driven linear actuator, a rack and pinion actuator, or the like installed on the gantry 30, thereby pressing the breasts 2.

Hereinafter, the operation of the all-in-one mammography and breast ultrasonography apparatus according to the present invention having such a configuration will be described.

Referring to FIGS. 1 to 4 and 12, the height of the scanning table 50 is adjusted by elevating the gantry 30 so that the subject can put the breasts 2 on the upper surface of the cover 52 in a comfortable posture. After the subject places the breasts 2 on the scanning table 50, the press plate 130 is moved down to press the breasts 2. By pressing the breasts 2 in this way, it is possible to enhance the sensitivity, accuracy and consistency of ultrasonography for a breast lump.

Figure 12A:
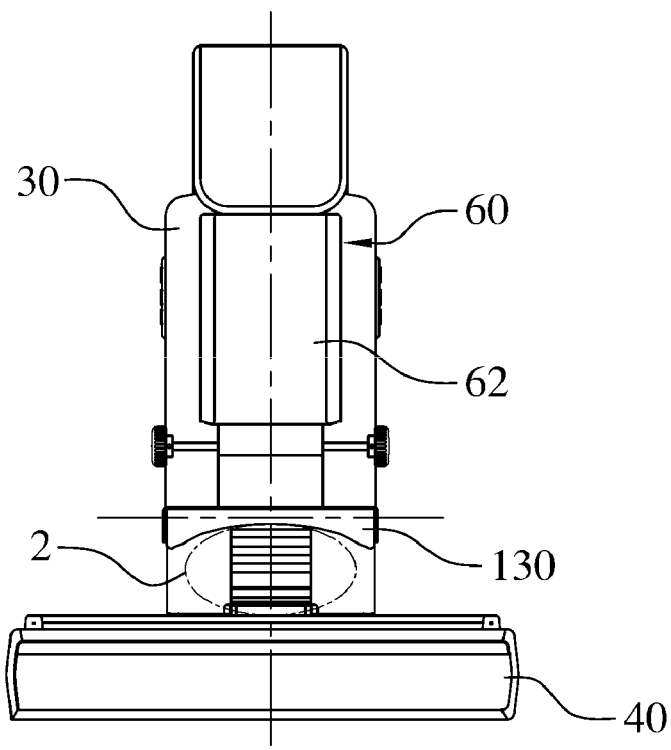
FIGS. 12A, 12B and 12C are views showing a zero state of the apparatus according to the present invention.
Figure 12B:
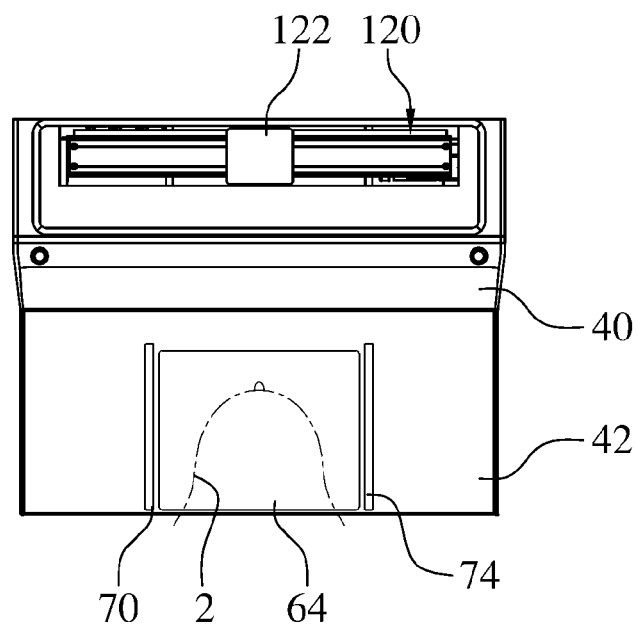
Figure 12C:
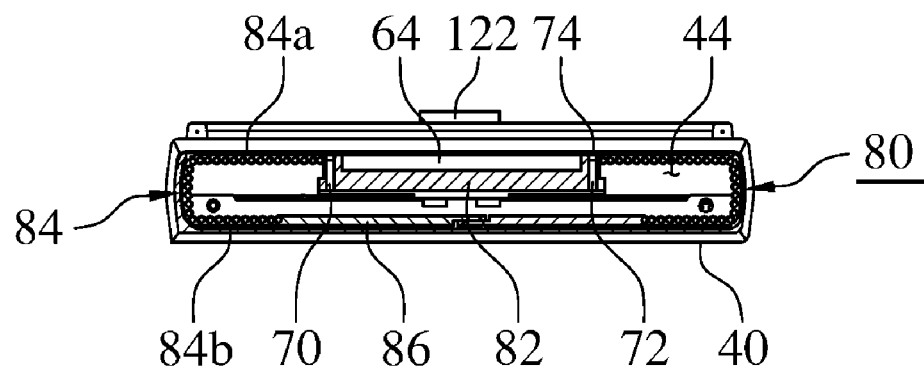

Referring to FIGS. 12 to 14, the mammography using the X-ray imaging device 60 and the breast ultrasonography using the first and second ultrasound probes 70 and 72 are performed by cranio-caudal (CC) view imaging and mediolateral oblique (MLO) view imaging as standard imaging methods. The cranio-caudal (CC) view imaging is performed while the breasts 2 are pressed up and down by the scanning table 40 and the press plate 130. The mediolateral oblique (MLO) view imaging is a method of imaging the breasts 2 at an angle of 30 to 60 degrees and includes left mediolateral oblique (LMLO) view imaging and right mediolateral oblique (RMLO) view imaging.

Figure 13A:
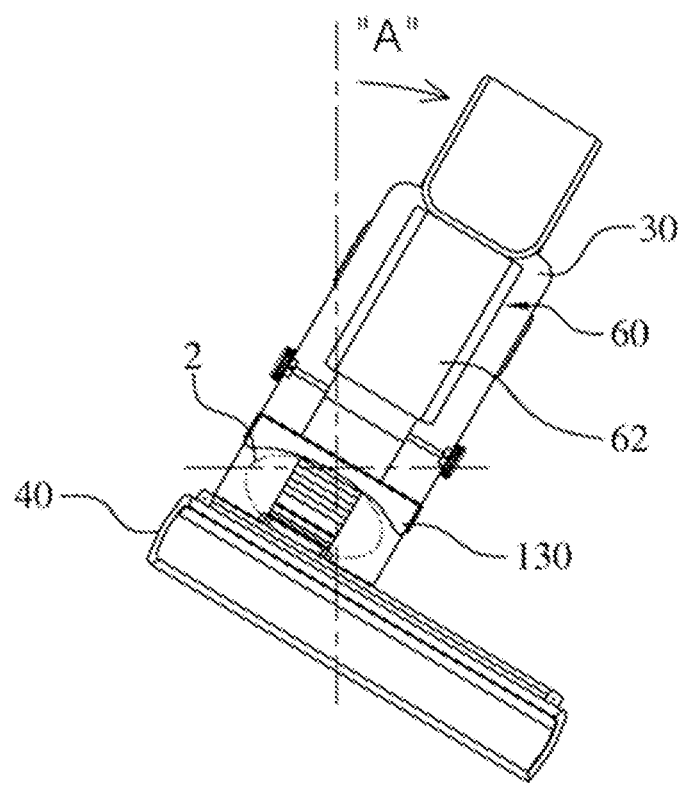
FIGS. 13A, 13B and 13C are views illustrating a left mediolateral oblique imaging state of the apparatus according to the present invention.
Figure 14A:
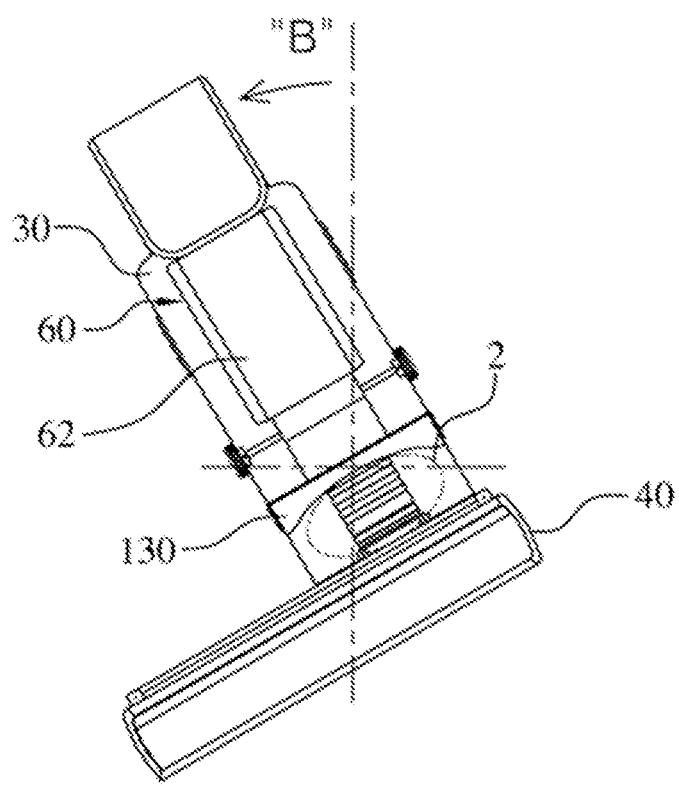
FIGS. 14A, 14B and 14C are views illustrating a left mediolateral oblique imaging state of the apparatus according to the present invention.

FIG. 12A shows a zero state of the gantry 30 in which the gantry 30 is vertically arranged and the central ray of the X-rays irradiated from the X-ray source 62 and the center of the X-ray flat panel detector 64 are aligned. In the zero state of the gantry 30, cranio-caudal (CC) view imaging for the breasts 2 may be performed. FIG. 13A shows LMLO view imaging in which the left side of each of the breasts 2 is imaged in a state in which the gantry 30 is rotated counterclockwise by about 45 degrees as indicated by arrow "A". FIG. 14A shows RMLO view imaging in which the right side of each of the breasts 2 is imaged in a state in which the gantry 30 is rotated clockwise by about 45 degrees as indicated by arrow "B".

The apparatus 10 according to the present invention can easily and accurately perform mediolateral oblique (MLO) view imaging for the side surfaces of the of the breasts 2 and the armpits by means of the X-ray imaging device 60 and the first and second ultrasound probes 70 and 72. This mediolateral oblique (MLO) view imaging is one of mammography that is basically performed to examine the enlarged lymph glands extending downward from the armpits as an early cause of breast cancer.

Figure 13B:
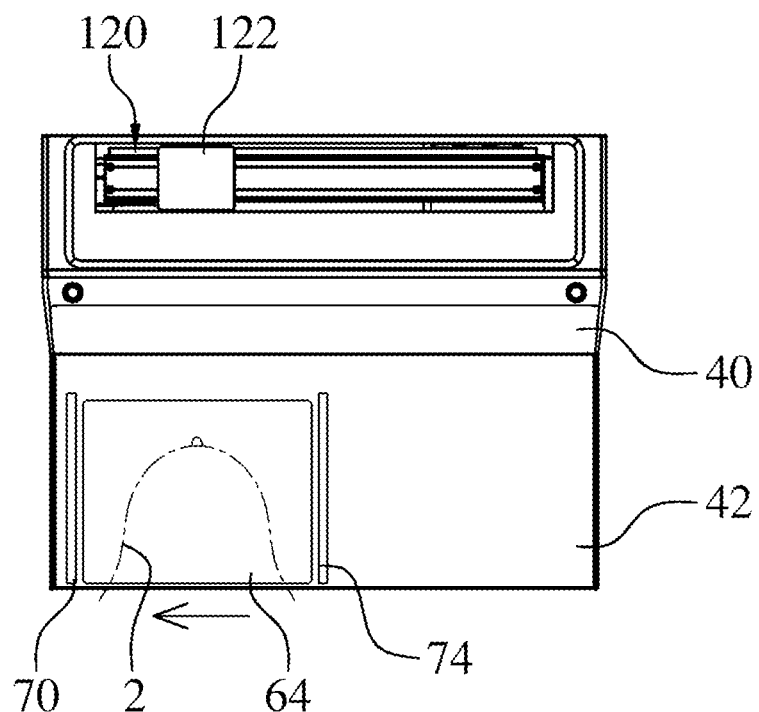
Figure 14B:
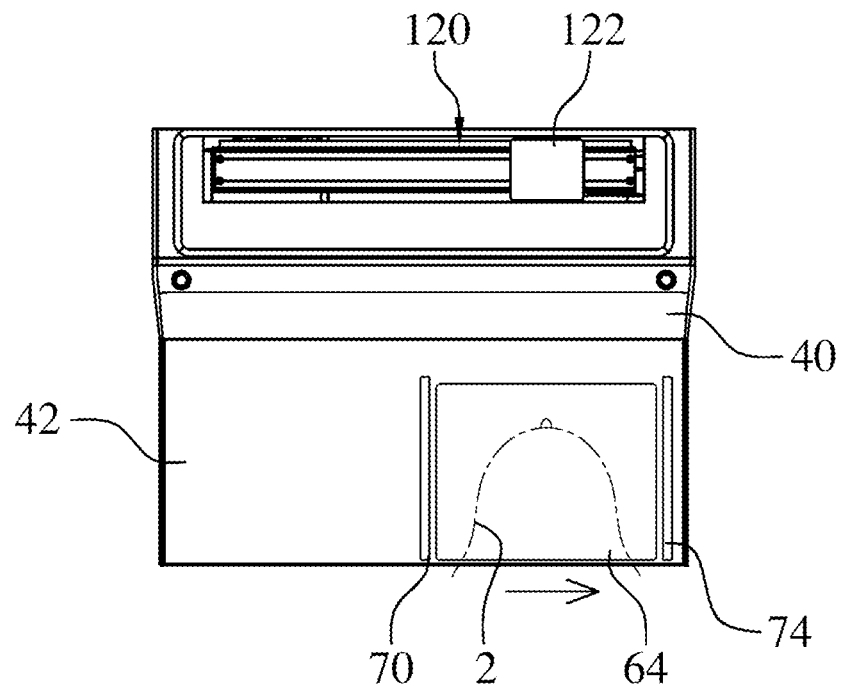

Referring to FIGS. 13B and 14B, during the MLO view imaging, the scanning table 40 is moved to the left or right based on the zero state of the gantry 30 by the operation of the table positioning actuator 120. The breast 2 is aligned with the rotation center of the gantry 30 by the scanning table 40 being moved to the left or right. In addition, while reducing the scanning distance of the first and second ultrasound probes 70 and 72, it is possible to expand the breast ultrasonography range and improve the examination efficiency.

Figure 13C:
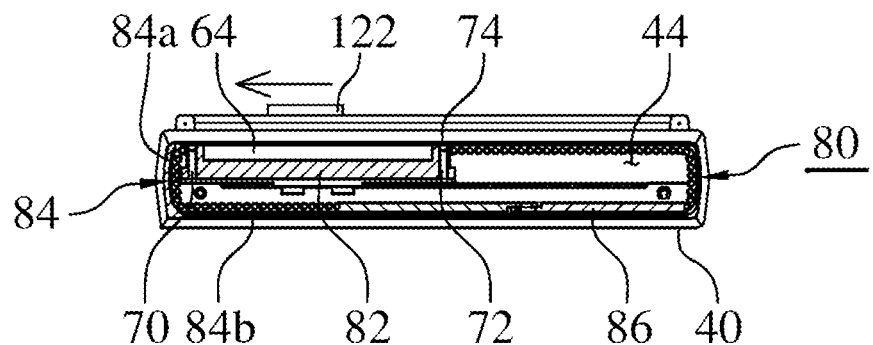
Figure 14C:
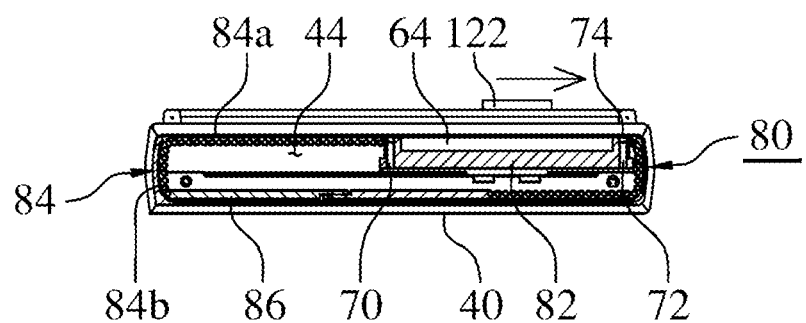

Referring to FIGS. 6 and 9 to 11, when the driving motor 92a is driven to rotate the driving pulleys 92b to scan the breasts 2, the belts 92d wound between the driving pulleys 92b and the driven pulleys 92c are caused to travel by the rotation of the driving pulleys 92b. As the belts 92d travel, the belts 92d and the fixed caterpillars 84 are orbitally moved to move the carriage 82 along the first axis X2, thereby moving the X-ray flat panel detector 64 and the first and second ultrasound probes 70 and 72 together. As shown in FIGS. 13B and 13C, during the LMLO view imaging, the first ultrasound probe 70 previously moved to the left side of the scanning table 40 is moved to the right side to scan the left side of the breast 2. As shown in FIGS. 14B and 14C, during the RMLO view imaging, the second ultrasound probe 72 previously moved to the right side of the scanning table 40 is moved to the left side to scan the right side of the breast 2. In this way, the right and left sides of the breast 2 can be accurately imaged while simultaneously moving the first and second ultrasound probes 70 and 72 along the first axis X2 by the operation of the orbital motion device 80 during the MLO view imaging. In addition, the scanning distance of the first and second ultrasound probes 70 and 72 can be reduced to shorten the imaging time, and the size and weight of the scanning table 40 and the orbital motion device 80 can be reduced to improve the operability.

Meanwhile, the X-rays irradiated by the operation of the X-ray source 42 pass through the window 132 of the press plate 130, the breasts 2, the gel pad 134 and the cover 52 and are detected by the X-ray flat panel detector 64. The signals detected by the X-ray flat panel detector 64 are displayed as X-ray images on the display 24 through image processing in the computer device 22.

The ultrasound waves transmitted from the reception/transmission surface 74 by the operation of the first and second ultrasound probes 70 and 72 are irradiated to the breasts 2, reflected from the breasts 2, and then received by the reception/transmission surface 74. The signals received by the first and second ultrasound probes 70 and 72 are displayed on the display 30 as ultrasound images through image processing by the computer program. When the mammography and the breast ultrasonography are completed, the press plate 130 is moved up by the operation of the vertical linear actuator 130 to release the pressure from the breasts 2.

In the apparatus 10 according to the present invention, the X-ray flat panel detector 64 and the first and second ultrasound probes 70 and 72 are mounted on the carriage 82 of the orbital motion device 80 so as to move toward or away from the breasts 2 pressed between the scanning table 50 and the press plate 130. This makes it possible to accurately know the coordinate values of the X-ray images acquired by the X-ray flat panel detector 64 and the coordinate values of the ultrasound images acquired by the ultrasound probes 70 and 72. Accordingly, the accuracy of breast cancer diagnosis may be enhanced by precisely matching the X-ray image and the ultrasound image through the processing in the computer device 32.

The embodiment described above is merely illustrative of a preferred embodiment of the present invention. The scope of the present invention is not limited to the described embodiment. Those skilled in the art may make various changes, modifications, or substitutions within the technical spirit of the present invention and the claims. Such changes, modifications, or substitutions should be understood to fall within the scope of the present invention.

What is claimed is:

1. An all-in-one mammography and breast ultrasonography apparatus, comprising: a scanning table on which breasts are placed, the scanning table having a first axis aligned with a scanning direction of the breasts and a second axis orthogonal to the first axis; an X-ray imaging device including an X-ray source arranged above the scanning table to generate X-rays for mammography and an X-ray flat panel detector arranged on the scanning table to detect the X-rays generated from the X-ray source; first and second ultrasound probes arranged on the scanning table so as to be adjacent to both ends of the X-ray flat panel detector to perform breast ultrasonography, the first and second ultrasound probes elongated along the second axis; and an orbital motion device installed on the scanning table to reciprocate the X-ray flat panel detector and the first and second ultrasound probes together along the first axis, wherein the orbital motion device includes: a carriage arranged on the scanning table to reciprocate along the first axis and having an upper surface on which the X-ray flat panel detector is mounted and on which the first and second ultrasound probes are mounted so as to be adjacent to both ends of the X-ray flat panel detector; a pair of caterpillars connected at one ends to both ends of the carriage so as to reciprocate the carriage along the first axis and including a plurality of links elongated along the second axis; a pair of sliding plates arranged on the scanning table to reciprocate along the first axis and connected to the other ends of caterpillars; and a horizontal linear actuator configured to drive the caterpillars along the first axis.

2. The apparatus of claim 1, wherein the X-ray flat panel detector and the first and second ultrasound probes are arranged on an arbitrary horizontal plane flush with a scanning surface of the scanning table.

3. The apparatus of claim 1, further comprising:
a press plate arranged between the X-ray source and the scanning table so as to press the breasts against the scanning table and configured to transmit the X-rays irradiated from the X-ray source.

4. The apparatus of claim 3, wherein the scanning table, the X-ray source and the press plate are mounted on a vertically movable and rotatable gantry.

5. The apparatus of claim 4, further comprising:
a table positioning linear actuator arranged behind the scanning table to translationally move the scanning table along the first axis, the table positioning linear actuator connected to the gantry.

6. The apparatus of claim 1, wherein the scanning table includes a flat cover mounted on an upper surface thereof and capable of transmitting the X-rays irradiated from the X-ray source.

7. The apparatus of claim 1, wherein the scanning table has a sealed chamber configured to accommodate the X-ray flat panel detector, the first and second ultrasound probes and the orbital motion device, and the chamber is filled with a liquid for propagating ultrasound waves.

8. The apparatus of claim 1, wherein the caterpillars connected to the carriage have upper portions flatly arranged on an arbitrary horizontal plane flush with upper surfaces of the X-ray flat panel detector and the first and second ultrasound probes so as to support the breasts pressed against the scanning surface.

9. The apparatus of claim 1, wherein the horizontal linear actuator includes: a belt transmission device mounted on the scanning table along the first axis to provide a driving force for orbital motion of the caterpillars; and a horizontal linear motion guide mounted on the scanning table to guide the sliding plates to reciprocate in a linear motion along the first axis.

10. The apparatus of claim 1, further comprising: an inner frame configured to be mounted on the scanning table while holding the carriage, the caterpillars, the sliding plates and the horizontal linear actuator.

11. The apparatus of claim 1, wherein each of the caterpillars includes an upper track connected to both ends of the carriage and flatly arranged on an upper side, and a lower track arranged below the upper track at a distance from the upper track and connected to the sliding plates, and the inner frame includes front and rear spacer plates mounted between both ends of the upper track and the lower track to maintain a gap between the upper track and the lower track.

* * * * *